(12) United States Patent
Koulen

(10) Patent No.: US 9,872,647 B2
(45) Date of Patent: Jan. 23, 2018

(54) DETECTION OF EARLY STAGE ALZHEIMER'S DISEASE AND MILD COGNITIVE IMPAIRMENT

(71) Applicant: The Curators of the University of Missouri, Columbia, MO (US)

(72) Inventor: Peter Koulen, Kansas City, MO (US)

(73) Assignee: The Curators of the University of Missouri, Columbia, MO (US)

( * ) Notice: Subject to any disclaimer, the term of this patent is extended or adjusted under 35 U.S.C. 154(b) by 197 days.

(21) Appl. No.: 14/844,898

(22) Filed: Sep. 3, 2015

(65) Prior Publication Data

US 2016/0302712 A1    Oct. 20, 2016

Related U.S. Application Data

(60) Provisional application No. 62/149,267, filed on Apr. 17, 2015.

(51) Int. Cl.
*A61B 3/024*   (2006.01)
*A61B 3/113*   (2006.01)
(Continued)

(52) U.S. Cl.
CPC .......... *A61B 5/4088* (2013.01); *A61B 3/0025* (2013.01); *A61B 3/0091* (2013.01);
(Continued)

(58) Field of Classification Search
CPC ....... A61B 5/40; A61B 5/4076; A61B 5/4088; A61B 5/6821; A61B 5/72; A61B 5/74; A61B 5/742; A61B 5/1075; A61B 3/00; A61B 3/0016; A61B 3/0025; A61B 3/0091; A61B 3/02; A61B 3/022; A61B 3/024; A61B 3/06; A61B 3/063; A61B 3/10; A61B 3/1005; A61B 3/102; A61B 3/113; A61B 3/1225; A61B 6/02; A61B 6/022; A61B 6/03; A61B 6/032; A61B 6/52; A61B 6/5211; A61B 6/5217; A61B 8/10; A61B 8/13; A61B 8/15; A61B 90/36; A61B 90/37; G06F 19/34; G06T 7/0012
(Continued)

(56) References Cited

U.S. PATENT DOCUMENTS

| 5,345,944 | A | * | 9/1994 | Hongo | A61B 3/113 600/555 |
| 2003/0160943 | A1 | * | 8/2003 | Xie | A61B 3/102 351/209 |
| 2011/0046480 | A1 | * | 2/2011 | Yonezawa | A61B 3/102 600/425 |

OTHER PUBLICATIONS

Pervin K. et al.,"Relationship between Cognitive Impairment and Retinal Morphological and Visual Functional Abnormalities in Alzheimer Disease", J Neuro-Ophthalmol, vol. 26, No. 1, 2006, p. 18-24.*

* cited by examiner

*Primary Examiner* — Thomas K Pham
*Assistant Examiner* — Ibrahima Diedhiou
(74) *Attorney, Agent, or Firm* — Shook, Hardy & Bacon L.L.P.

(57) ABSTRACT

Systems and methods are described herein for determining that a patient has indications mild cognitive impairment (MCI) or early stage Alzheimer's disease (AD). Microperimetry is used to assess the functional integrity of the patient's retina. Optical Coherence Tomography is used to assess the structural integrity of the patient's retina. Reductions in the size and function of the patient's retina indicate that the patient may have MCI or early stage AD.

13 Claims, 10 Drawing Sheets
(3 of 10 Drawing Sheet(s) Filed in Color)

(51) Int. Cl.
*A61B 5/00* (2006.01)
*A61B 3/00* (2006.01)
*A61B 3/10* (2006.01)
*A61B 3/12* (2006.01)
*A61B 5/107* (2006.01)

(52) U.S. Cl.
CPC .............. *A61B 3/024* (2013.01); *A61B 3/102* (2013.01); *A61B 3/1005* (2013.01); *A61B 3/113* (2013.01); *A61B 3/1225* (2013.01); *A61B 5/1075* (2013.01); *A61B 5/7282* (2013.01); *A61B 5/6821* (2013.01)

(58) Field of Classification Search
USPC ....... 351/200, 205, 206, 209, 211, 222, 224, 351/239, 246
See application file for complete search history.

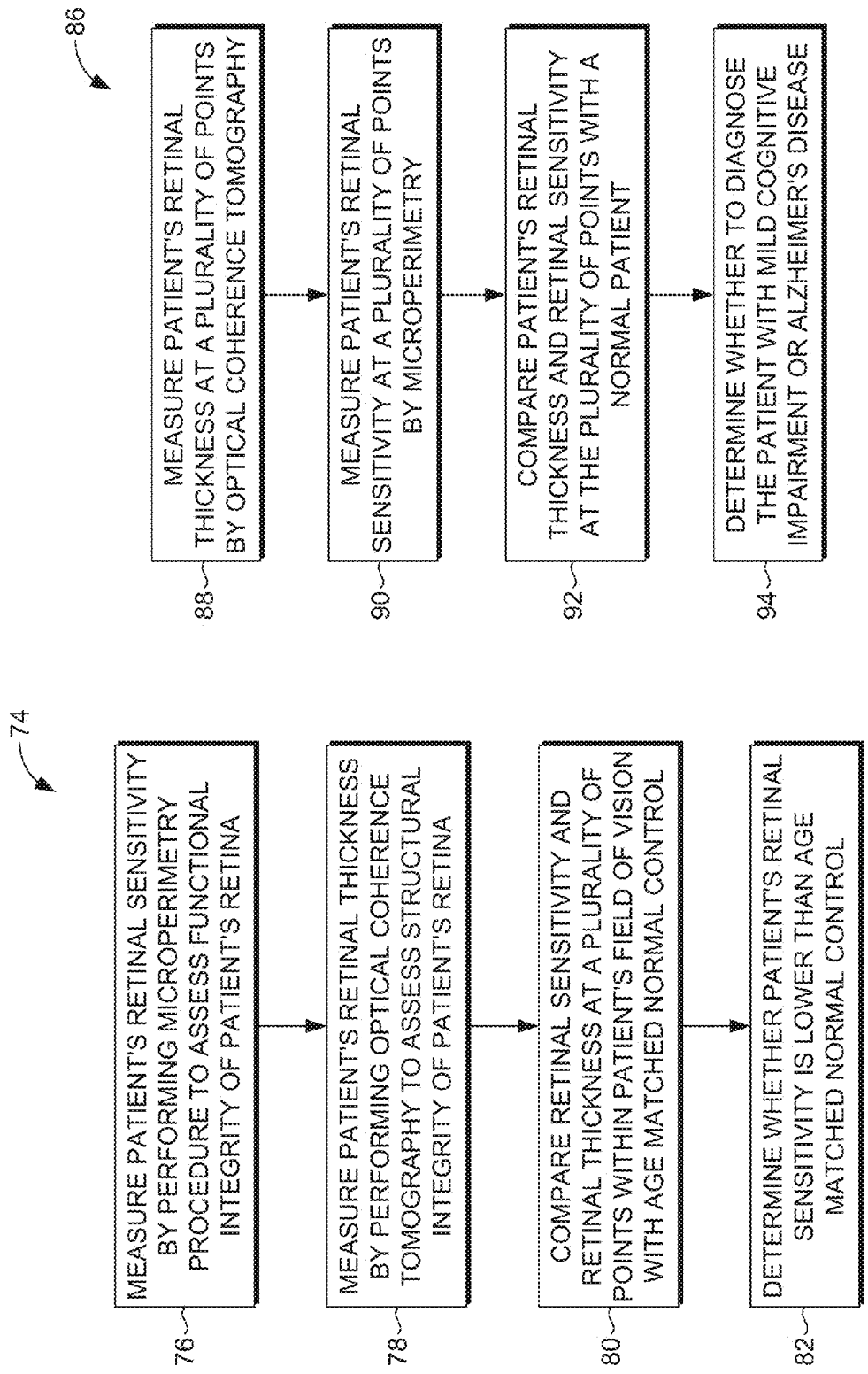

DETECTION OF EARLY STAGE ALZHEIMER'S DISEASE AND MILD COGNITIVE IMPAIRMENT

CROSS-REFERENCE TO RELATED APPLICATIONS

This application claims priority to U.S. Provisional Application No. 62/149,267, filed Apr. 17, 2015 and entitled "DETECTION OF EARLY STAGE ALZHEIMER'S DISEASE." The entirety of the aforementioned application is incorporated by reference herein.

GRANT STATEMENT

None.

FIELD OF THE INVENTION

The present invention relates to the field of Alzheimer's disease detection, most specifically to an early-stage detection method using microperimetry.

BACKGROUND OF THE INVENTION

Seven million Americans are affected by Alzheimer's disease (AD), which is the 6th leading cause of death in the US. However, early diagnosis of AD and mild cognitive impairment are extremely difficult due to the complete lack of accepted detection methods and the difficulty to screen for early disease reliably and unambiguously. Since the retina is both functionally as well as developmentally part of the central nervous system, there is good rationale to expect structural and functional changes in the retina similar to the rest of the brain in AD patients. Previous clinical studies have also shown that changes in the structure and function of the retina occur in AD patients. However, no detection method for early-stage AD has been successfully developed.

Microperimetry is an FDA-approved diagnostic tool used in ophthalmology to diagnose various eye-related diseases. Microperimetry assesses the functional integrity of a patient's retina. Optical Coherence Tomography (OCT) is used to assess the structural integrity of a patient's retina.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods and systems for early-stage detection of Alzheimer's disease (AD). Clinical studies have shown that changes in the structure and function of the retina occur in AD patients. In exemplary aspects, a microperimeter is used to assess the functional integrity of a patient's retina by measuring the patient's retinal sensitivity to light stimuli of defined size and intensity. The patient's retina is imaged by optical coherence tomography (OCT) to assess the structural integrity of the patient's retina. OCT can be used to create a three-dimensional representation of a patient's retina and to measure structural aspects of the retina such as thickness. Both of these procedures may be performed sequentially to measure structural and functional changes in the retina at the same time, for example in the context of eye examinations performed by physicians. The retinal sensitivity and retinal thickness of the patient's retina is determined at a plurality of points within the patient's central field of vision. These values are compared to an age matched control of the same gender based on patients without AD. This comparison may be done with a computer having at least one processor.

If the patient's retinal sensitivity and/or retinal thickness are reduced compared to the control, a physician may determine that the patient should be diagnosed with AD or its precursor, mild cognitive impairment (MCI). A further measure indicative of early stage AD is eye movement fixation pattern data. Fixation of the eye is measured by microperimetry, along with retinal sensitivity. If the patient's fixation is reduced compared to the age matched control, this may be an indication of early stage MCI or AD.

BRIEF DESCRIPTION OF THE DRAWINGS

Embodiments are described in detail below with reference to the attached drawing figures. The patent or application file contains at least one drawing executed in color. Copies of this patent or patent application publication with color drawing(s) will be provided by the Office upon request and payment of the necessary fee.

FIG. 9 is a flow diagram of an exemplary method of early detection of Alzheimer's disease, in accordance with one embodiment of the invention; and FIG. 10 is a flow diagram of an exemplary method of diagnosing mild cognitive impairment or early stage Alzheimer's disease in a patient, in accordance with one embodiment of the invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to computerized methods and systems for early detection of Alzheimer's disease (AD) or mild cognitive impairment (MCI) in a patient. A technique known as microperimetry is utilized to measure how well a patient's vision responds to defined light stimuli. Measurements are taken at multiple points within the patient's field of vision. This determines whether the patient's retinal sensitivity to defined light stimuli is reduced compared to a normal, age-matched subject of the same gender. In addition, Optical Coherence Tomography (OCT) is utilized to measure the patient's retinal thickness.

Figure 1:
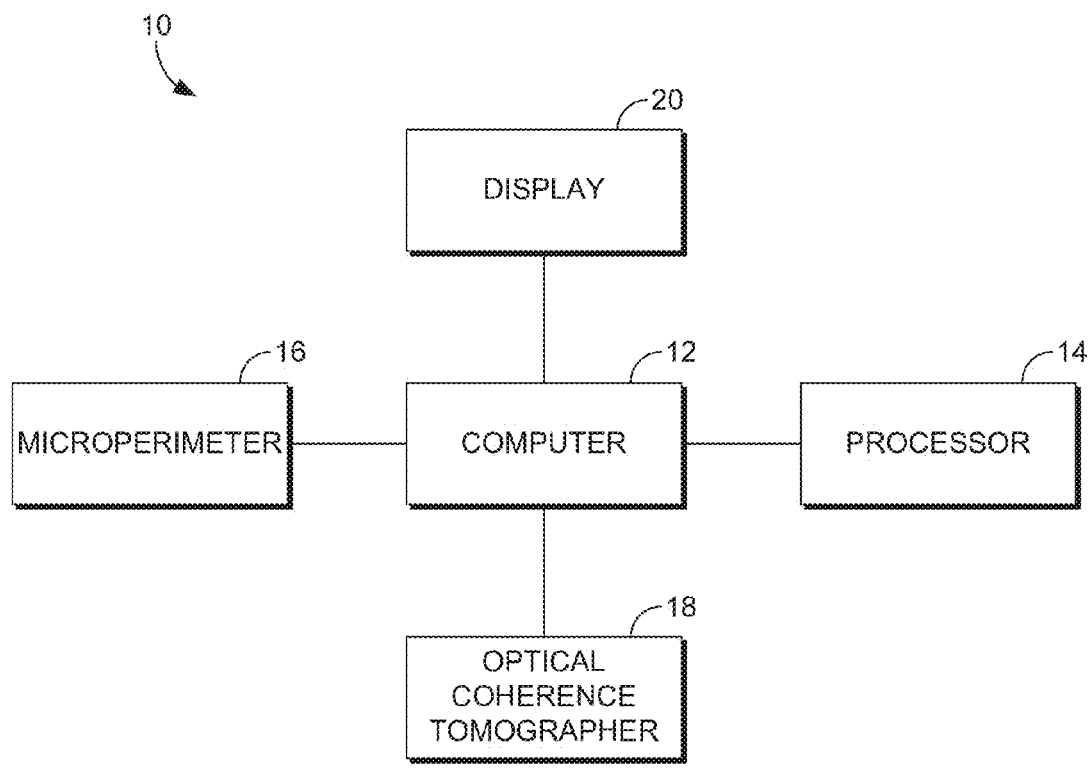
FIG. 1 is a diagram of an exemplary system for screening a patient for Alzheimer's disease and mild cognitive impairment, in accordance with one embodiment of the invention.

Turning to FIG. 1, an exemplary computing system 10 for screening a patient with AD or MCI is shown. The system comprises a computer 12 having at least one processor 14. The computing system is merely an example of one suitable computing system and is not intended to suggest any limitation as to the scope of use or functionality of embodiments of the present invention. Neither should the computing system be interpreted as having any dependency or requirement related to any single module/component or combination of modules/components illustrated therein.

In some embodiments, one or more of the illustrated components/modules may be implemented as stand-alone applications. In other embodiments, one or more of the illustrated components/modules may be integrated directly into the computing system. The components/modules illustrated in FIG. 1 are exemplary in nature and in number and should not be construed as limiting. Any number of components/modules may be employed to achieve the desired functionality within the scope of embodiments hereof. Further, components/modules may be located on any number of servers.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The computer 12 receives retinal sensitivity data from a microperimeter 16. The computer 12 may also receive eye movement fixation pattern data from the microperimeter 16. The computer 12 also receives retinal thickness data from an optical coherence tomographer 18.

The computer 12 utilizes the processor 14 to compare the retinal sensitivity data and the retinal thickness data with an age matched control. The processor 14 may also compare the eye movement fixation pattern data with the age matched control.

Based on this comparing, the processor 14 determines whether to diagnose the patient with AD or MCI. This determination may include diagnosing a patient with AD or MCI when the retinal sensitivity data show a reduction in sensitivity in the center of the macula compared to the age matched control and the retinal thickness data shows a reduction in thickness of the center of the macula compared to the age matched control. More specifically, when the retinal sensitivity data shows a reduction in sensitivity of at least 20% of the inner macula and a reduction in sensitivity of at least 10% of the temporal, nasal, and inferior portions of the retina compared to the age matched control, the patient is diagnosed with Alzheimer's disease. This determining step may further include diagnosing a patient with AD or MCI when the eye movement fixation pattern data shows a reduction in fixation within the center 2° circle compared to the age matched control.

The system may also include a display 20 on which to display the results to a user. The display 20 may include a simple yes or no indication of whether the patient shows signs of early stage AD or MCI.

Figure 2A:
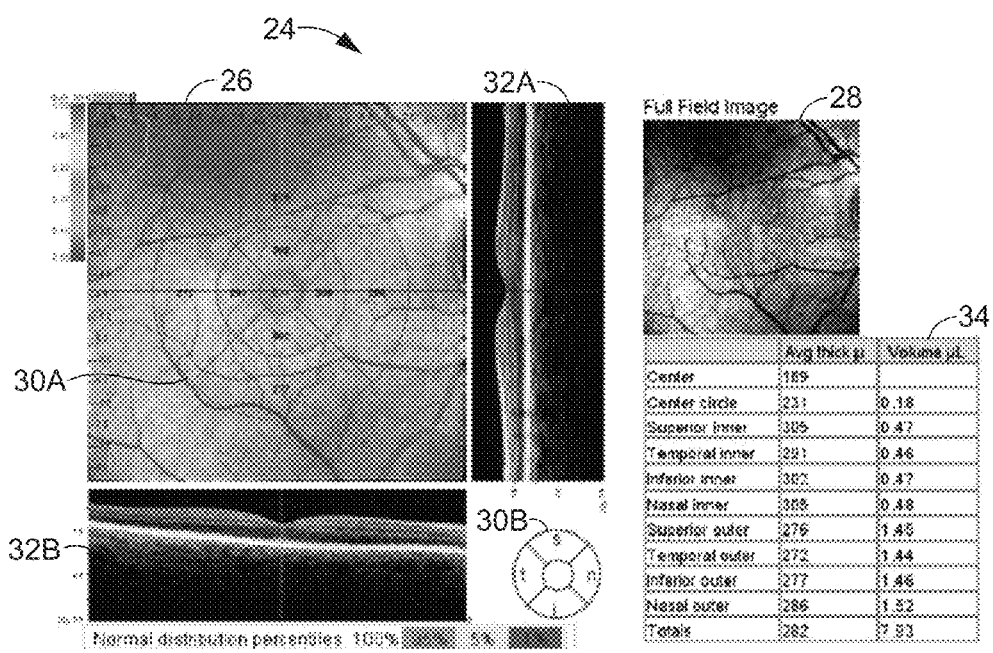
FIG. 2A is an exemplary OCT output from the system of FIG. 1.

Turning now to FIG. 2A, exemplary microperimetry and OCT output data 24 are shown. The box in the upper left corner 26 displays an OCT image of a patient's retina. The same retinal image is duplicated in a full field image 28 at the upper right of FIG. 2A. Blood vessels are visible in the retinal images. The blood vessels are used to track movement of the eye during the microperimetry readings.

A segmented, circular grid 30a overlays the retinal image. The center circle of the grid is centered over the macula in the center of the retina. The circular grid is divided into four regions. This grid 30b is reproduced to the lower right of the main retinal image. The regions are: superior (s), temporal (t), inferior (i), and nasal (n). Each region is divided into inner and outer segments.

Figure 2B:
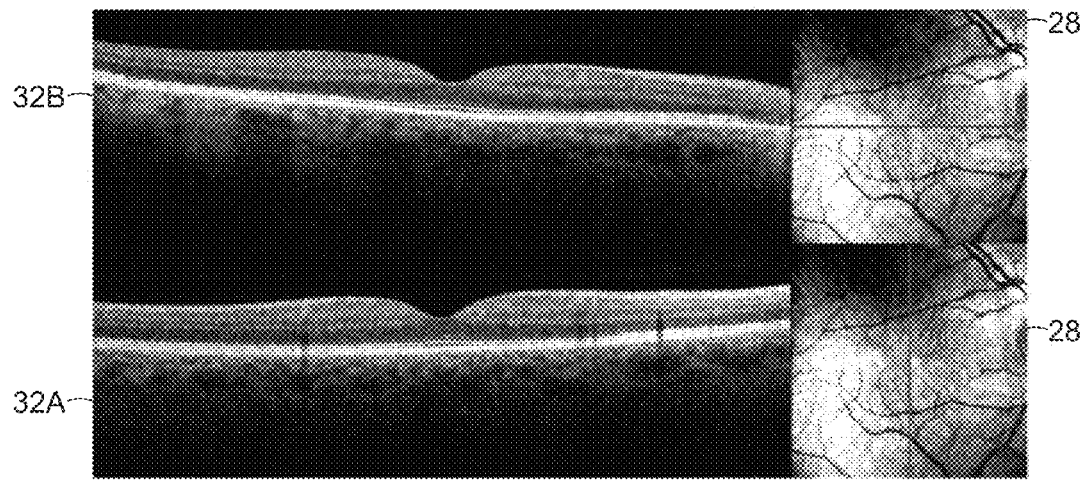
FIG. 2B is an enlarged view of the OCT output of FIG. 2A.

Cross-sectional images 32a, 32b of the patient's retina are displayed directly to the right and to the bottom of the retinal image. The entire retina is scanned to analyze its thickness and volume. Values for the average thickness and volume of each segment of the retina are displayed in the table 34 in the lower right portion of FIG. 2A. For example, the nasal inner segment of this patient's retina has an average thickness of 305 μm ("Avg thick μ") and a volume of 0.48 μL. These cross-sectional images 32a, 32b of the patient's retina are shown in an enlarged view in FIG. 2B. The full field images 28 to the right of the enlargement indicate the location of the cross-section with an arrow.

Figure 3A:
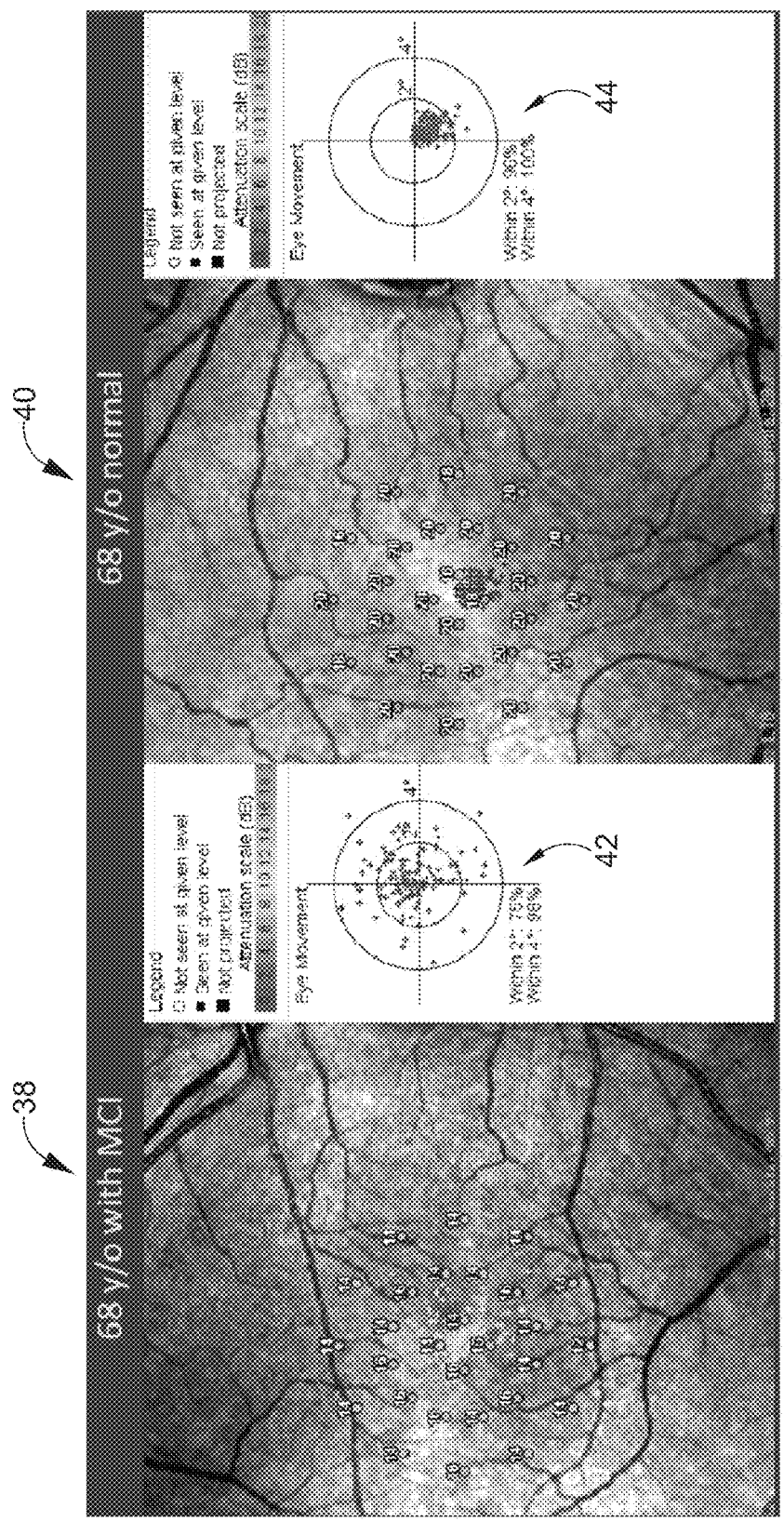
FIG. 3A is an exemplary microperimetry output from the system of FIG. 1 and depicts microperimetry readings and fixation patterns of the retina of a 68 year old individual with MCI on the left, and a 68 year old normal individual on the right.
Figure 3B:
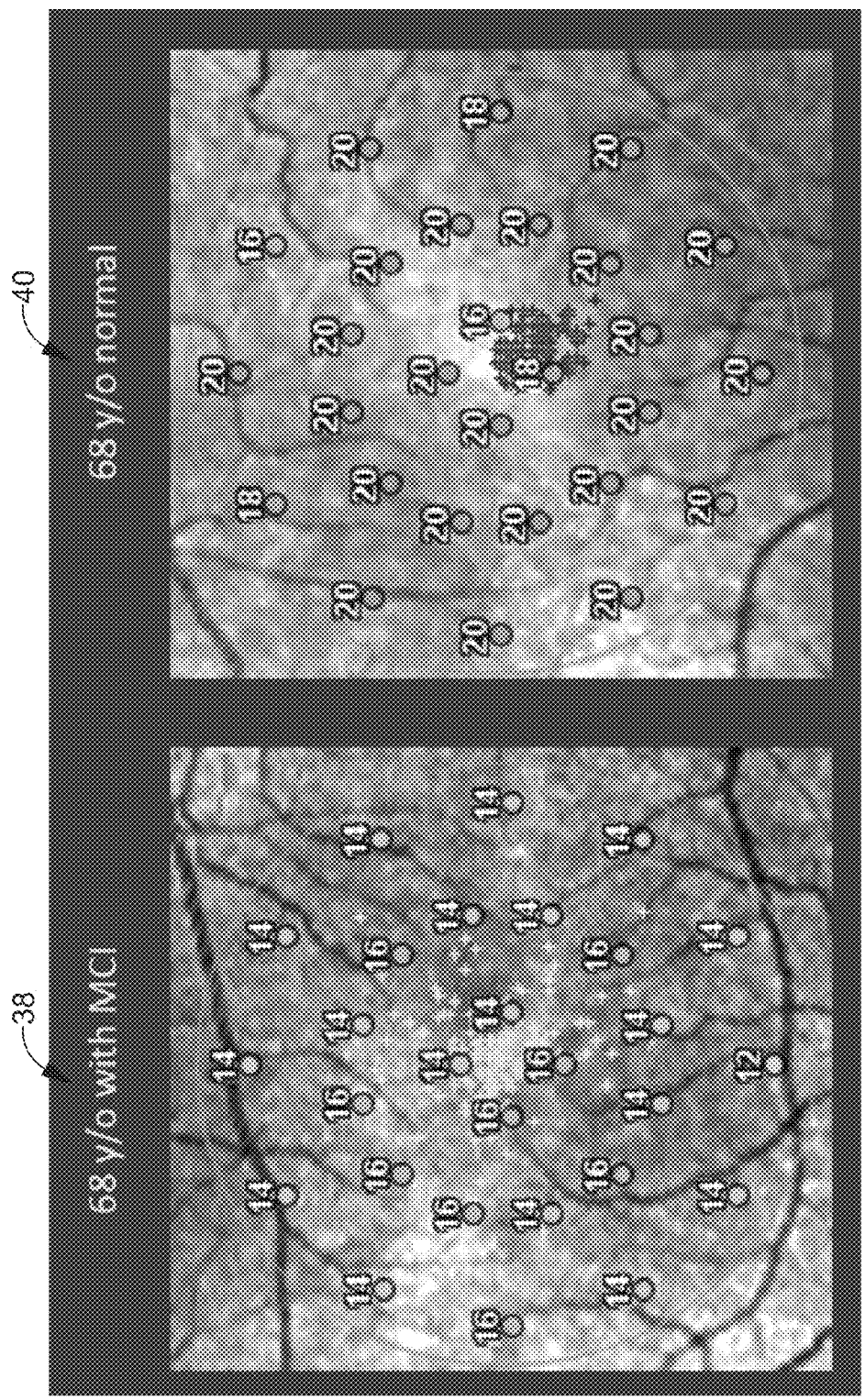
FIG. 3B shows an enlarged view of the microperimetry readings and fixation patterns of FIG. 3A.

Turning to FIG. 3A, microperimetry output data is displayed for a 68 year old with MCI (left) 38 and a normal 68 year old (right) 40. FIG. 3B shows enlarged views of the microperimetry output 38, 40 of FIG. 3A. Microperimetry measures the sensitivity of a patient's retina in order to assess the functional integrity of the retina. During the microperimetry procedure, the patient is presented with defined size spots of white light of differing defined luminance projected at various locations of the patient's retina. The location of the spot of light is chosen randomly within the retina. If the patient can see the spot of light, the patient presses a button to register the response. The points where light stimuli are presented are represented by circles in FIG. 3A. When the patient is presented with light at the dimmest luminance—20 decibels (dB) and if the patient can see the spot of light, that response is recorded as a closed circle over the location where the light was presented on the retina and labeled with "20." While 20 dB represents the dimmest luminance, 0 dB represents the brightest possible luminance in the output shown in FIG. 3. A normal subject is expected to register most or all of the points of light at 20 dB, as shown in the microperimetry output at the right 40 in FIG. 3A. If, however, the patient does not register the point of light at 20 dB, light stimuli with increasingly brighter luminance, i.e. a lower dB value, are presented to the patient at that location of the patient's retina until the patient registers the point of light. The patient may respond to the light stimuli at brightness levels of 14 dB or 16 dB if the patient has MCI, as shown in the exemplary microperimetry output at the left 38 in FIG. 3A.

In addition to assessing the patient's retinal sensitivity to light stimuli, microperimetry measures the patient's ability to fixate on a given point. While the microperimetry readings are being taken, the patient is instructed to look directly at the junction of two intersecting lines (represented by the cross in the circular grids 42, 44 shown to the right of each micrometry reading in FIG. 3A). The locations of the blood vessels in the patient's retina are used to track eye movement during the microperimetry procedure.

The patient's ability to fixate on the cross is assessed and plotted on the image with small crosses, as shown in the outputs 38, 40 of FIG. 3A. The patient's ability to fixate on a point is indicative of how well the patient can control eye movements and their focus on a specified region of the field of vision. As can be seen in the Eye Movement grids 42, 44 to the right of retinal images, the fixation patterns differ between MCI 42 and normal patients 44. In FIG. 3A, the fixation plot is much more scattered for the MCI patient 42 on the left than the normal patient on the right 44. The most marked difference is within the 2° circle of the grid. The MCI patient's fixation is 75% within 2° compared to 96% in the normal subject.

Figure 4:
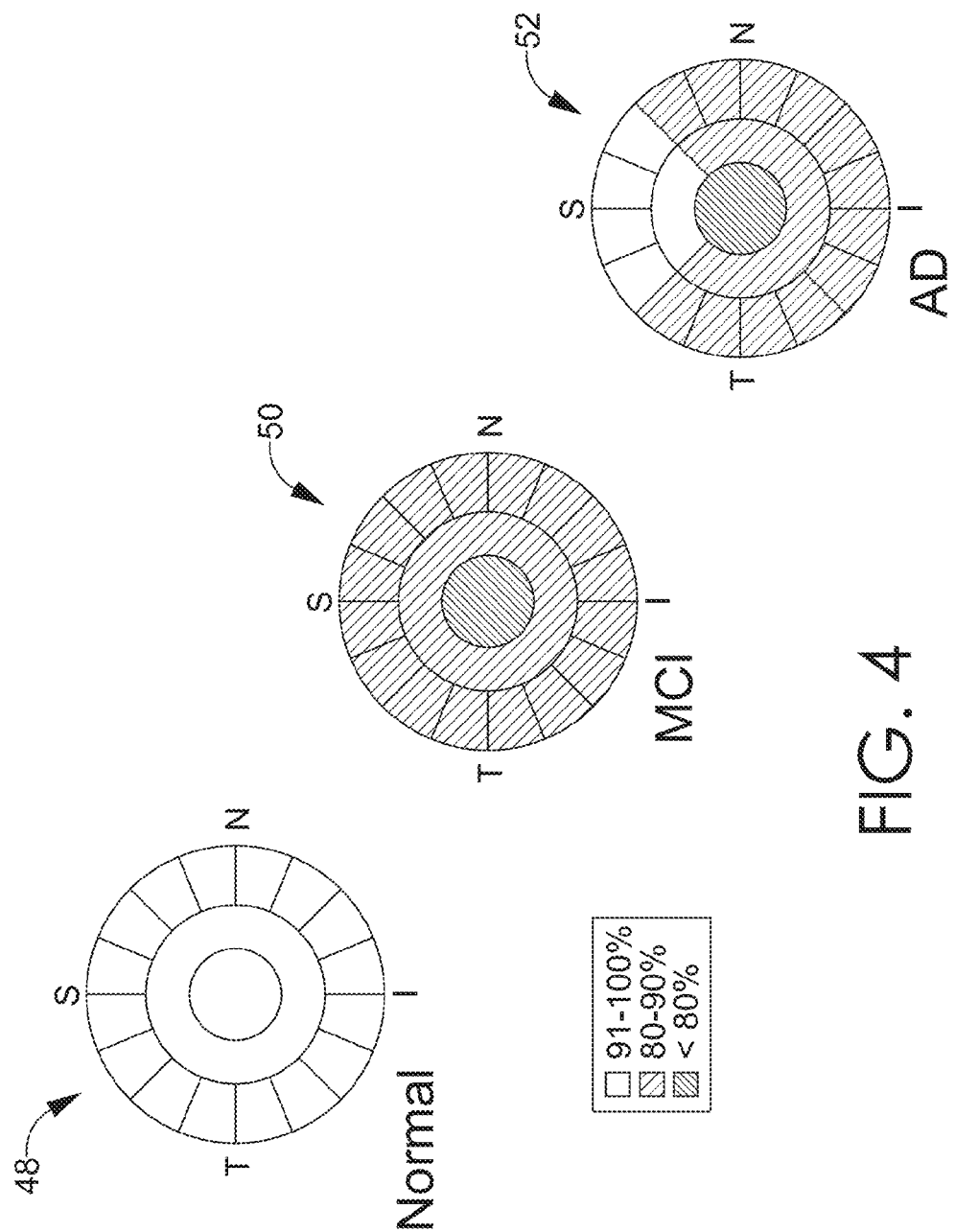
FIG. 4 is a diagram representing a summary of microperimetry outputs from the system of FIG. 1 quantifying the sensitivity of the center of the retina of normal patients (left), patients with MCI (middle), and patients with Alzheimer's disease (right)

FIG. 4 is a summary schematic of the reductions in macular sensitivity generally observed in normal, MCI, and AD patients. As can be seen in the left schematic for a normal patient 48, the entire retina has normal levels of sensitivity (91-100%). Patients with MCI experience an overall reduction of sensitivity in the retina of about 10% with greater reduction seen in the inner macula at the center (over 20%). Therefore sensitivity of the retina to light stimuli is less than 80% in the inner macula and 80-90% in other areas of the retina for MCI patients, as shown in the middle schematic 50. AD patients experience a similar reduction in sensitivity as MCI patients, except that the superior region of the retina has normal sensitivity levels (91-100%), as indicated in the schematic on the right 52.

Figure 5:
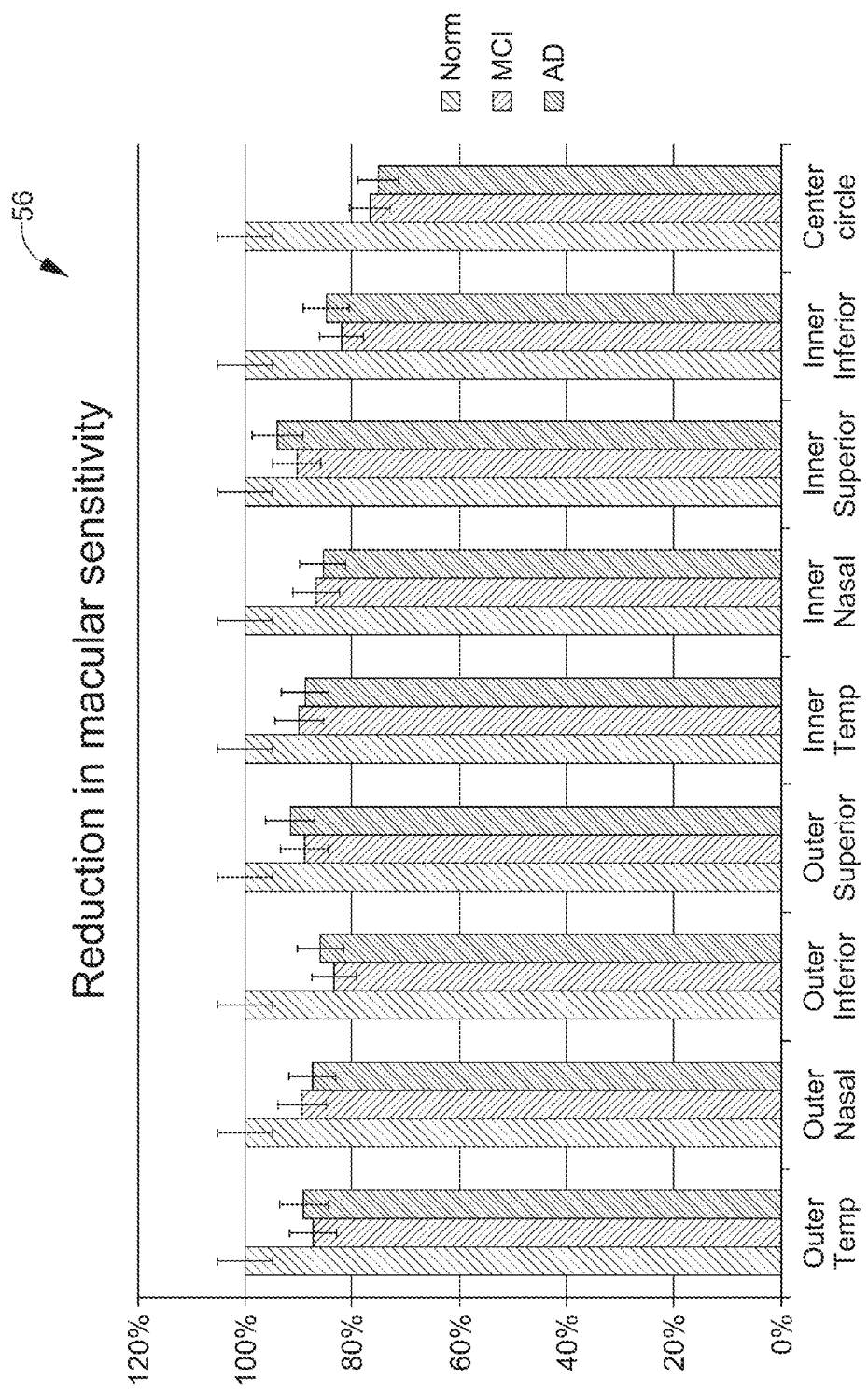
FIG. 5 depicts a bar graph of a summary of microperimetry outputs from the system of FIG. 1 quantifying a reduction in sensitivity of various portions of the center of the retina of normal patients (Norm), patients with MCI, and patients with AD.

FIG. 5 is a bar graph 56 comparing macular sensitivity data of normal patients, subjects with MCI, and patients with AD. Values are shown for each segment of the retina. As can be seen, macular sensitivity is reduced in all segments of the retina in both MCI and AD patients, compared to normal patients. There is a particularly strong reduction in macular sensitivity in the center circle (inner macula) of the retina in both MCI and AD patients.

Figure 6:
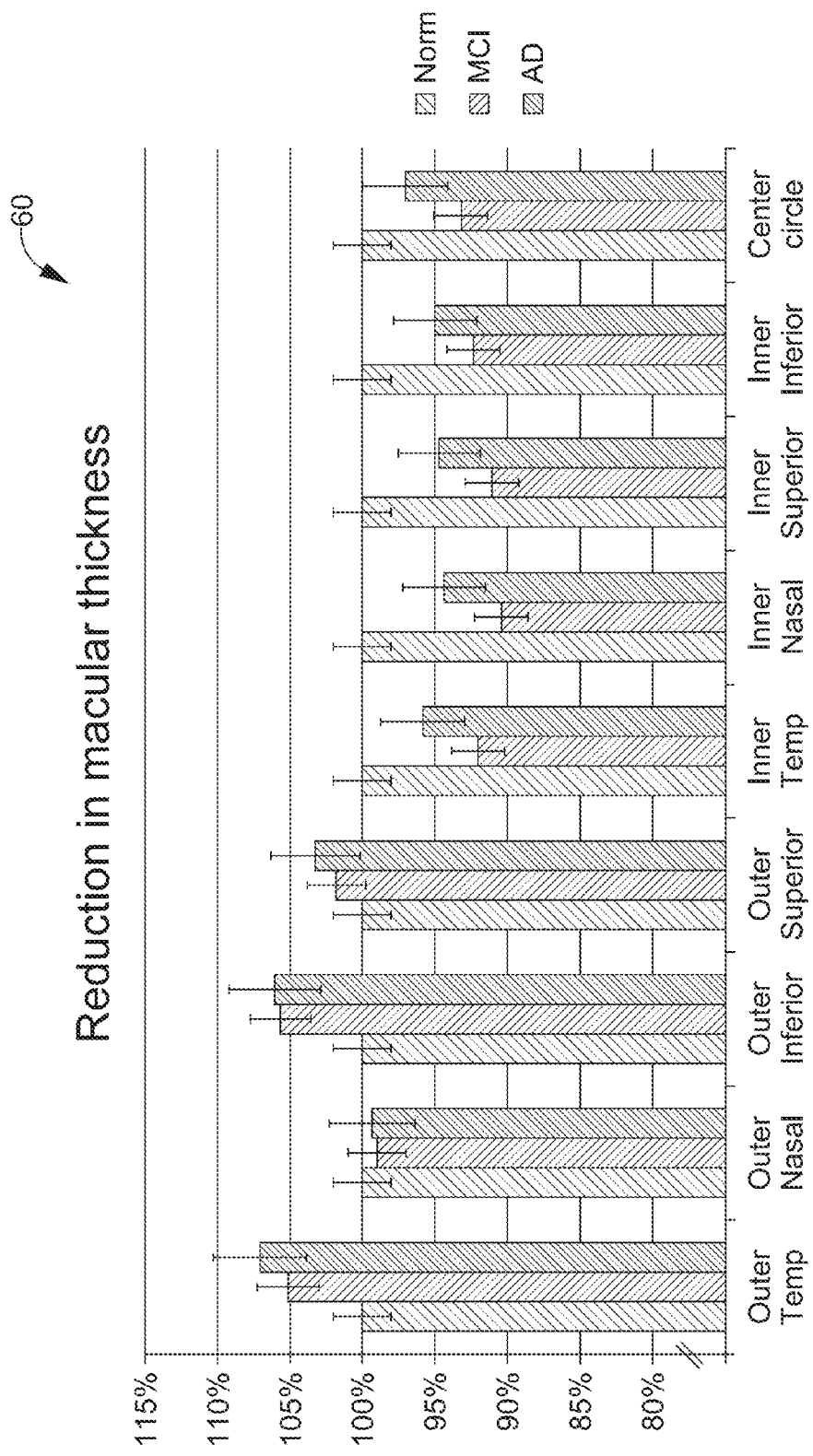
FIG. 6 depicts a bar graph of a summary of OCT outputs from the system of FIG. 1 quantifying a reduction in macular thickness of various portions of the central retina of normal patients (Norm), patients with MCI, and patients with AD.

FIG. 6 is a bar graph 60 comparing macular thickness data of normal patients, patients with MCI, and patients with AD. There is an overall pattern of reduced thickness in the inner segments of the retina and increased thickness in the outer segments of the retina in MCI and AD patients compared to normal patients.

Figure 7:
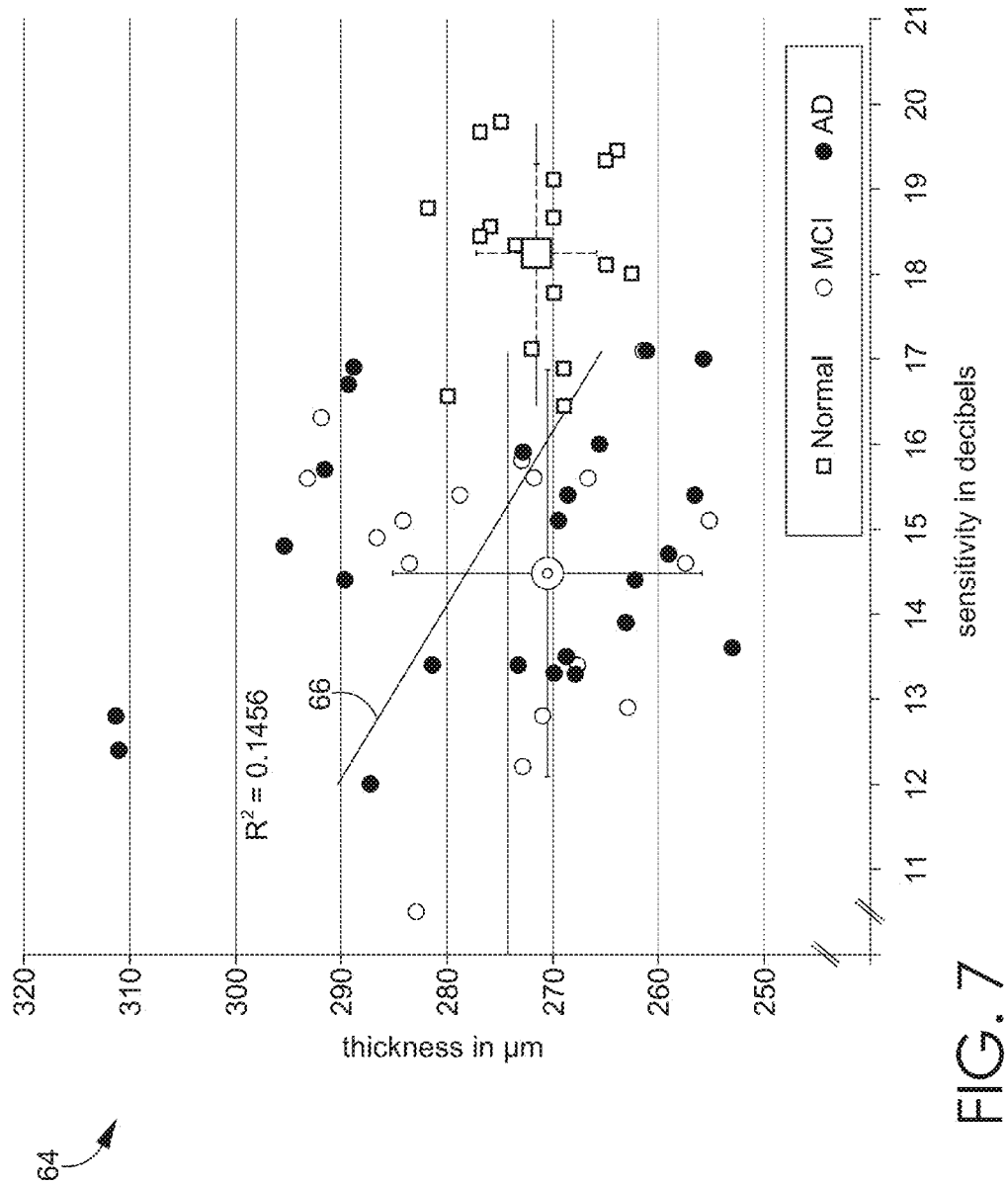
FIG. 7 depicts a scatter graph plotting macular thickness with the corresponding sensitivity of the central retina of normal patients, patients with MCI, and patients with AD.

FIG. 7 is a scatter graph 64 plotting values for thickness of retina (in µm) against values for sensitivity of retina (in decibels). Normal subjects are represented by open squares, MCI patients are represented by open circles, and AD patients are represented by closed circles. As can be seen from this graph, normal patients are distinguished from MCI and AD patients by a difference in retinal sensitivity. The trend line 66 applies to the linear correlation between thickness and sensitivity exhibited for AD patients with an $R^2=0.1456$. This correlation distinguishes AD patients from MCI patients as it is absent in MCI patients and normal subjects.

Figure 8:
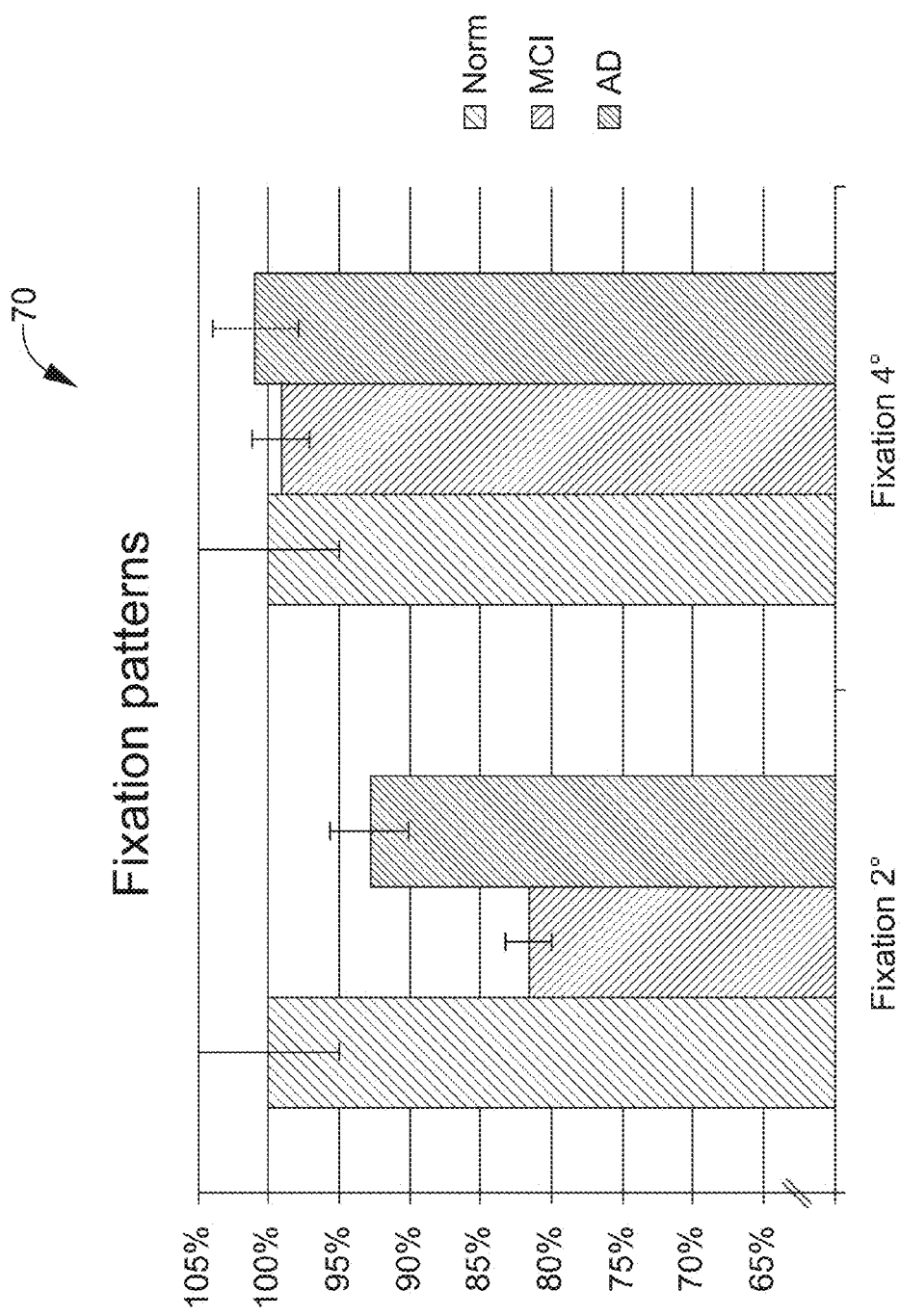
FIG. 8 depicts a bar graph of fixation patterns of the eyes in normal (Norm), MCI, and AD patients during the acquisition of microperimetry outputs from the system of FIG. 1 and quantifying the percentage of patients capable of maintaining adequate fixation in the center 2° or 4° circle of the stimulation pattern ("Fixation 2°" and "Fixation 4°," respectively)

FIG. 8 is a bar graph 70 comparing fixation patterns for normal subjects, patients with MCI, and patients with AD. The fixation patterns indicate the patients' ability to focus on the cross during the procedure, as described above. The data shows that fixation patterns within the 2° circle are reduced, particularly in MCI patients, compared to normal patients.

Turning now to FIG. 9, a flow diagram 74 of an exemplary computerized method for early detection of AD is shown. At a step 76, a patient's retinal sensitivity is measured by performing a microperimetry procedure to assess the functional integrity of the patient's retina. Microperimetry measures how well the patient's vision responds to defined light stimuli. At a step 78, the patient's retinal thickness is measured by performing optical coherence tomography to assess the structural integrity of the patient's retina. The patient's eye movement fixation may also be measured by the microperimetry procedure.

At a step 80, the retinal sensitivity and retinal thickness at a plurality of points within the patient's central field of vision are compared with those of age matched normal control subjects. Preferably, subjects of the same gender are used as the controls. The patient's fixation pattern may also be compared with control subjects. At a step 82, it is determined whether the patient's retinal sensitivity is lower than that of age matched normal control subjects.

Based on the determination that the patient's retinal sensitivity is lower than normal, the patient may then be diagnosed with AD or MCI based on the retinal sensitivity and retinal thickness levels of the patient. The patient may be diagnosed with MCI when the macular sensitivity of the center of the retina is reduced by at least 20% in the patient compared to normal controls. The patient may be diagnosed with AD when the macular sensitivity of the inner macular of the retina is reduced by at least 20% and the macular sensitivity of the inferior, nasal, and temporal portions of the retina are reduced by at least 10%.

FIG. 10 depicts a flow diagram 86 of an exemplary computerized method for diagnosing MCI or early stage AD in a patient. At a step 88, the patient's retinal thickness is measured at a plurality of points by optical coherence tomography. At a step 90, the patient's retinal sensitivity is measured at a plurality of points by microperimetry. Microperimetry measures the response of the patient's retina to defined light stimuli. The patient's eye movement may also be measured to determine a fixation pattern. The fixation pattern is determined by tracking movement of blood vessels on the patient's retina.

At a step 92, the patient's retinal thickness and retinal sensitivity at the plurality of points are compared with those of normal subjects. The normal patients are preferably of the same age and gender as the patient and do not have AD or MCI. The patient's fixation pattern may also be compared.

At a step 94, a determination is made whether to diagnose the patient with MCI or AD. This determination may be made when the patient's retinal sensitivity and retinal thickness are reduced compared to the normal patient. Additionally, this determination may be supported by a finding that the patient's fixation pattern shows a reduction in fixation within two degrees compared to the normal patient.

The patient may be diagnosed with mild cognitive impairment when the patient's macular sensitivity of the inner macular is reduced by at least 20% compared to the normal patient. The patient may be diagnosed with AD when the patient's macular sensitivity of the inner macula is reduced by at least 20% and the patient's macular sensitivity of the inferior, nasal, and temporal portions of the retina are reduced by at least 10% compared to the normal patient.

What is claimed is:

1. A computerized method carried out by at least one server having at least one processor for detection of mild cognitive impairment, the method comprising:
    measuring a patient's retinal sensitivity by performing a microperimetry procedure to assess the functional integrity of the patient's retina;
    comparing the retinal sensitivity at a plurality of points within the patient's field of vision with an age matched normal control;
    determining whether the patient's retinal sensitivity is lower than the age matched normal control, and
    determining that the patient has indications of mild cognitive impairment and recommending additional neurological evaluation,
    wherein the patient is determined to have indications of mild cognitive impairment when macular sensitivity of the center of the retina is reduced by at least 20%.

2. The computerized method of claim 1, further comprising measuring the patient's retinal thickness by performing optical coherence tomography to assess the structural integrity of the patient's retina and comparing the retinal thickness at a plurality of points within the patient's field of vision with the age matched normal control.

3. The computerized method of claim 1, further comprising measuring the patient's ability to fixate eye movement and vision on a given pattern and comparing the patient's ability to fixate within a predefined region around the given pattern with an age matched normal control.

4. A system for screening a patient for Alzheimer's disease or mild cognitive impairment, the system comprising:
    a microperimeter;
    an optical coherence tomographer;
    a computer having at least one processor, wherein the computer performs the following steps:
    (A) receiving retinal sensitivity data from the microperimeter,
    (B) receiving retinal thickness data from the optical coherence tomographer,
    (C) comparing, with the at least one processor, the retinal sensitivity data and retinal thickness data with age and gender matched control subjects, and
    (D) based on the comparing, determining, with the at least one processor, whether to diagnose the patient with Alzheimer's disease or mild cognitive impairment, wherein the determining comprises diagnosing a patient with Alzheimer's Disease or mild cognitive impairment when the retinal sensitivity data shows a reduction in sensitivity in the inner macula compared to the age and gender matched control subjects and the retinal thickness data shows a reduction in thickness of the inner macula compared to the age and gender matched control subjects, and wherein the diagnosing a patient with Alzheimer's Disease or mild cognitive impairment comprises diagnosing the patient with Alzheimer's Disease when the retinal sensitivity data shows a reduction in sensitivity of at least 20% of the inner macula and a reduction in sensitivity of at least 10% of the inferior, temporal, and nasal portions of the retina compared to the age and gender matched control subjects.

5. The system of claim 4, wherein the computer further performs the step of receiving eye movement data from the microperimeter identifying the patient's ability to fixate eye movement and vision on a pattern, and comparing, with the at least one processor, the eye movement fixation pattern data with an age matched control.

6. The system of claim 5, wherein determining further comprises diagnosing a patient with Alzheimer's Disease or mild cognitive impairment when the eye movement fixation pattern data shows a reduction in fixation compared to the age and gender matched control subjects.

7. A computerized method carried out by at least one server having at least one processor for determining that the patient has indications of early stage Alzheimer's disease, the method comprising:
    measuring the patient's retinal sensitivity at a plurality of points by microperimetry;
    comparing the patient's retinal sensitivity at the plurality of points with that of normal patients; and
    determining, based on the comparing, the patient has indications of Alzheimer's disease, wherein the determining comprises finding the patient has indications of Alzheimer's Disease when the patient's macular sensitivity of the inner macula is reduced by at least 20% and the patient's macular sensitivity of the inferior, nasal, and temporal portions of the retina are reduced by at least 10% when compared to the normal patients.

8. The computerized method of claim 7, further comprising measuring the patient's retinal thickness at a plurality of points by optical coherence tomography and comparing the patient's retinal thickness at the plurality of points with that of normal patients.

9. The computerized method of claim 7, wherein the normal patients are of the same age and gender as the patient and do not have Alzheimer's disease or mild cognitive impairment.

10. The computerized method of claim 7, wherein determining comprises finding a patient has indications of Alzheimer's Disease or mild cognitive impairment when the patient's retinal sensitivity and retinal thickness are reduced compared to the normal patients.

11. The computerized method of claim 7, further comprising measuring the patient's eye movement to determine a fixation pattern and comparing the patient's fixation pattern with the normal patients.

12. The computerized method of claim 11, wherein determining further comprises finding a patient has indications of mild cognitive impairment or Alzheimer's Disease when the patient's fixation pattern shows a reduction in fixation within two degrees compared to the normal patients.

13. The computerized method of claim 11, wherein the fixation pattern is determined by measuring eye movement using the tracking of blood vessels in the patient's retina.

* * * * *